United States Patent [19]
Grana et al.

[11] 4,089,209
[45] May 16, 1978

[54] REMOTE WATER MONITORING SYSTEM

[75] Inventors: David C. Grana; David P. Haynes, both of Newport News, Va.

[73] Assignee: The United States of America as represented by the Administrator of the National Aeronautics and Space Administration, Washington, D.C.

[21] Appl. No.: 821,681

[22] Filed: Aug. 4, 1977

[51] Int. Cl.² ............................................... G01N 1/10
[52] U.S. Cl. .................................. 73/61 R; 73/170 A; 73/425.4 R
[58] Field of Search ..................... 73/61 R, 53, 170 A, 73/61.1 R, 425.4 R, 421 R

[56] References Cited

U.S. PATENT DOCUMENTS

| | | | |
|---|---|---|---|
| 3,214,964 | 11/1965 | Davis | 73/53 |
| 3,339,417 | 9/1967 | Richard | 73/170 A |
| 3,489,012 | 1/1970 | Niskin | 73/425.4 R |

*Primary Examiner*—Anthony V. Ciarlante

*Attorney, Agent, or Firm*—Wallace J. Nelson; John R. Manning; Howard J. Osborn

[57] ABSTRACT

A remote water monitoring system is described that integrates the functions of sampling, sample preservation, sample analysis, data transmission and remote operation. The system employs a floating buoy carrying an antenna connected by lines to one or more sampling units containing several sample chambers. Receipt of a command signal actuates a solenoid to open an intake valve outward from the sampling unit and communicates the water sample to an identifiable sample chamber. Such response to each signal receipt is repeated until all sample chambers are filled in a sample unit. Each sample taken is analyzed by an electrochemical sensor for a specific property and the data obtained is transmitted to a remote sending and receiving station. Thereafter, the samples remain isolated in the sample chambers until the sampling unit is recovered and the samples removed for further laboratory analysis.

7 Claims, 5 Drawing Figures

REMOTE WATER MONITORING SYSTEM

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

This invention relates generally to apparatus for sampling a liquid medium and more particularly to remotely located apparatus for obtaining samples at discrete points in time, analyzing the samples, transmitting data while the apparatus remains submerged, and preserving the samples for laboratory analysis.

In water body research considerable difficulties have been experienced in the interpretation of remote measurements, particularly in measuring changes in water quality, mainly because of the problems of correlating surface measurements with actual conditions. A primary reason for this poor correlation is the lag time between obtaining a sample and its analysis. The chemical and biological characteristics of a sample may be altered drastically if the time interval between sample taking and sample analysis becomes excessive. Further, water conditions can vary, for example with the tide or time of day, these changes being unnoticed unless discrete samples are taken over a period of time at the same location.

Closely associated with the deterioration of a sample with time is the taking of a false sample. Prior sampling devices have had an external cavity surrounding a valved sample entranceway. Stagnant water collecting in this cavity may not be representative of the actual water conditions at the time a sample is taken, but nonetheless constitute a portion of the water sample taken.

Another problem associated with sample devices capable of providing on-site analysis is accurate control of the volume of water constituting each sample. Certain sensors require that sample volume be controlled in order to obtain useful information. It is further necessary that all volumes are consistent where a number of samples are taken at various times and comparisons are made between the samples.

Clearly there is a need in the art for a water monitoring apparatus which is capable of remote operation and which is able to take a number of samples of constant volume representative of the surrounding water body when taken. Furthermore, there is need for an apparatus capable of specimen analysis while submerged; capable of transmitting the data obtained to a surface location and which also preserves the samples for on-shore examination.

Therefore, it is an object of the present invention to provide a water monitoring device which takes representative water samples at desired intervals.

It is a further object of the present invention to provide a water monitoring device which takes a plurality of samples, each of a controlled volume, and stores them for above-surface examination.

It is another object of the present invention to provide a water monitoring device capable of sample analysis while remaining submerged.

It is an additional object of the present invention to provide a water monitoring device which takes samples upon command from a remote surface station.

It is a further additional object of the present invention to provide a water monitoring device which provides data from sample analysis to a remote surface station while remaining submerged.

SUMMARY OF THE INVENTION

These and other objects are obtained in the present invention by providing a remotely controlled water monitoring system having a novel valved sampling apparatus which eliminates the collecting cavity of prior devices and accurately controls the volume of the water sample taken. The present invention consists of a device which incorporates apparatus for remotely sampling, analyzing and collecting water specimens into a single, self-sufficient unit which furthermore provides for the retention of each discrete sample in a controlled environment after in-unit analysis to accommodate more extensive laboratory analysis when desired or if transmitted data indicates such a need.

Specifically the present invention consists of a submersible sampling unit containing a number of sample chambers, each having a solenoid actuated valve. The unit also contains a battery-powered control module connected to the valve solenoids for their activation and to sensors in each sample chamber for the collection of data.

A buoy, attached to the sample unit by a hollow connection hose, has an antenna affixed to its top for signal receipt and transmission with a remote sending and receiving station which are communicated through leads running down through the connection hose to the control module.

Each valve and sample chamber pair includes a spool valve having an entrance barrel extending through the sample unit periphery. The barrel is sealed by a spool shaft and end cap, the end of the spool shaft being flared to close off the barrel passageway while the end cap covers the barrel end. The remainder of the shaft extends into the barrel and is of a smaller diameter than the barrel. The spool shaft seats against a movable piston controlled by a solenoid and return spring assembly. Activation of the solenoid causes the piston to move toward the sampling unit periphery forcing the spool shaft to unseat and extend into the water, allowing water to pass into the valve barrel where it is vented to the sample chamber. The end cap and flared shaft end, when seated, operate to eliminate cavities where water could collect and stagnate, and when extended, operate to remove marine growth attached to the surface of the sampling unit from the path of inflowing water. This assures each sample is representative of the water body when taken.

Each chamber contains a liquid level switch having a float on a rod and wired into the solenoid circuit. Inflow of water causes the float to rise along the rod. Upon water volume reaching a set level within the sample chamber, permanent magnets in the ball float cause a reed-type switch to be thrown thereby cutting power to the activated valve solenoid. The piston is returned to its original position by the return spring causing the spool shaft and end cap to again seat against the valve barrel, preventing further water ingress and limiting the sample in the chamber to the desired volume.

Once a chamber has received a water sample, a sensor is utilized to analyze for a particular property and transfer the data collected to the control module which transmits the data via the float antenna to a remote receiving station. An example of the particular property of interest would be the coliform bacteria level in each sample. If such were the case, a dual electrode capable of measuring changes in voltage level could comprise the sensor. By placing a specific quantity of lauryl tryptose broth in each sample chamber prior to submersion of the sampling unit, the number of coliform bacteria originally in each sample becomes determinable since it is directly proportional to the time required for the organisms to produce sufficient hydrogen from their consumption of the nutrient broth to cause a predetermined potential to exist in the chamber measureable by the dual electrodes. This analytical method is more fully described in U.S. Patent No. 4,009,078 to Wilkins et al. The time interval between sample taking and the change in potential comprises the data sent to the remote receiver station.

The control module of the present invention is capable of sequentially activating each solenoid. It furthermore, is able to store data and respond upon interrogation with a data transmission pertaining to the sample contained in each sample chamber. Thus, the sample unit can be commanded to take a number of samples according to a desired schedule; then respond with data for each chamber on a periodic basis.

Additionally, once a sample is taken it remains in its respective sample chamber until the sample unit is raised to the surface and the sample chambers removed. This permits each sample to remain in a controlled environment facilitating laboratory analysis should this be desired upon retrieval.

In summary, the present invention discloses apparatus the combination of which performs the functions of remotely sampling, analyzing and collecting water specimens by a single self-sufficient unit. A novel valve and sample chamber apparatus assures that representative samples of a controlled volume are taken and remain in a controlled environment.

Finally, the unit can be interrogated while still in position to provide data pertaining to each sample to a remote on-shore location.

BRIEF DESCRIPTION OF THE DRAWINGS

A more complete appreciation of the invention and many of the attendant advantages thereof will be readily apparent as the same becomes better understood by reference to the following detailed description when considered in connection with the accompanying drawings, wherein.

DETAILED DESCRIPTION

Figure 1:
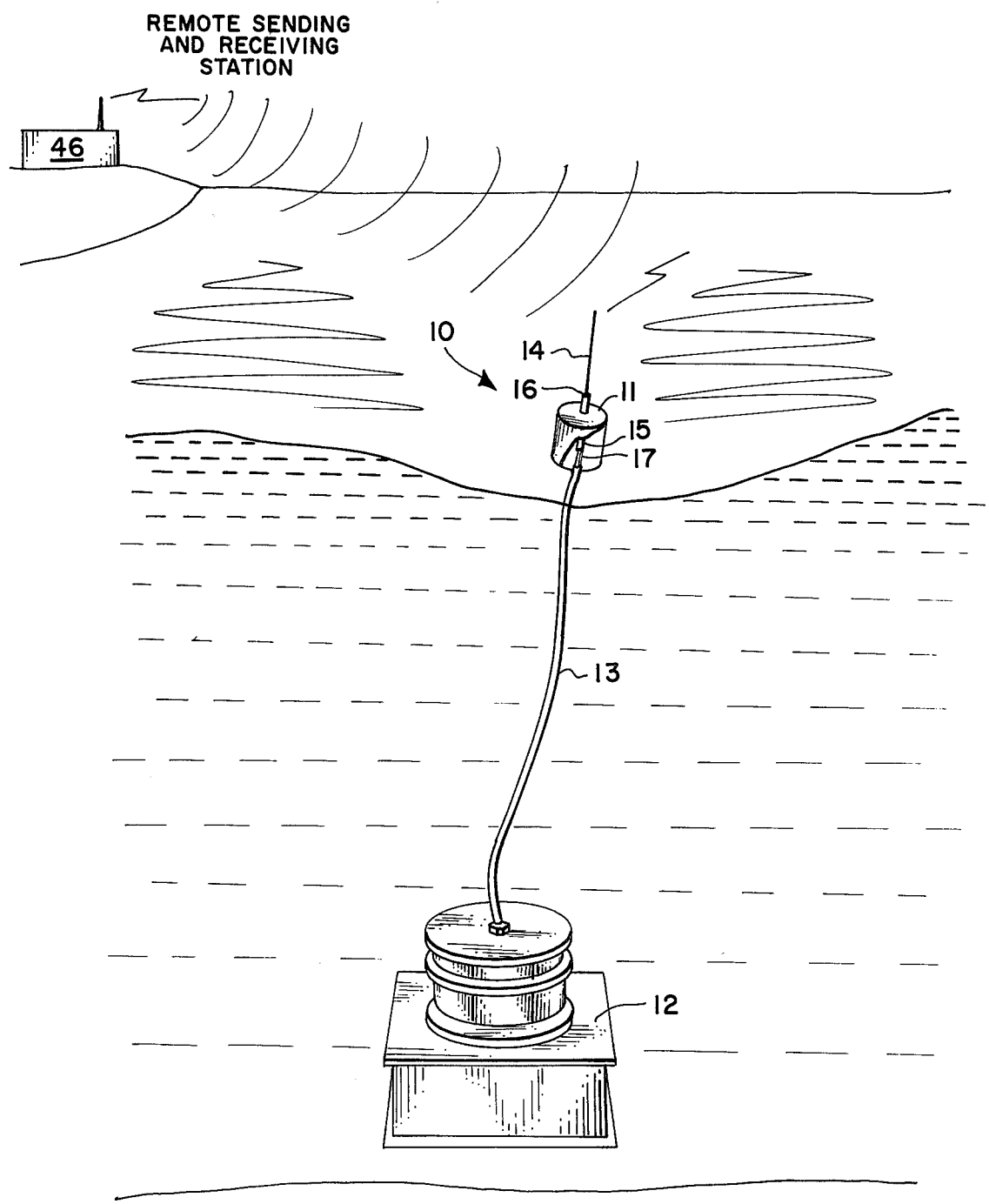
FIG. 1 is a perspective of the remote water monitoring device showing the sampling unit submerged to the water bed and connected to the floating marker buoy housing the receiving and transmitting antenna.

Referring now to the drawings wherein like reference numerals designate identical parts throughout the several views, there is shown a remote water monitoring system embodying the present invention, and generally designated by reference numeral 10.

Figure 2:
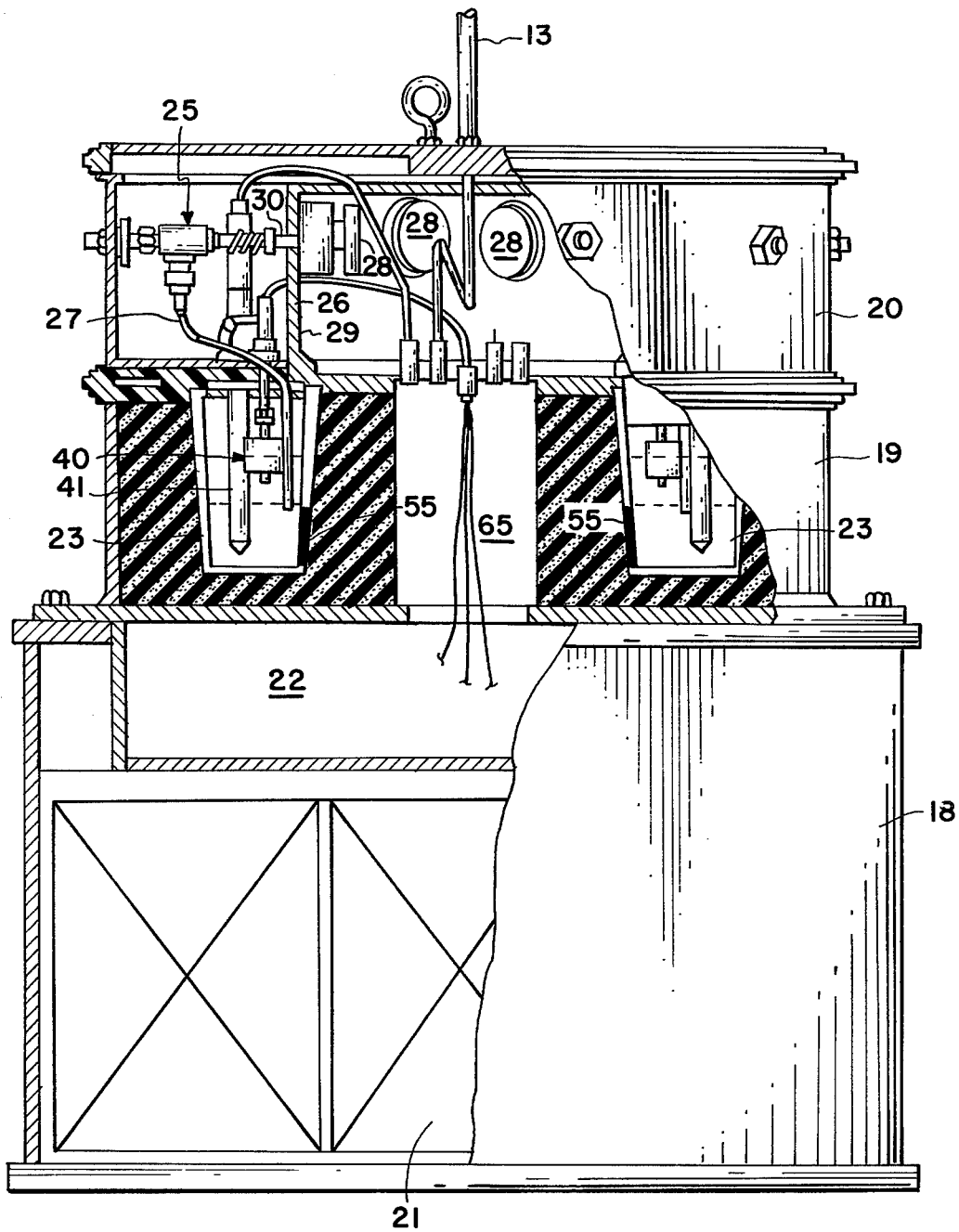
FIG. 2 is a front view cutaway of the sampling unit exposing a portion of the contained sampling, analysis, and sending and receiving apparatus.

As shown in FIG. 1 the present invention has two major components, buoy 11 and sample unit 12, connected to one another by a hollow flexible hose 13. When in position, sample unit 12 sits against the bottom while buoy 11 floats on the water surface. Hose 13 is of sufficient length to allow buoy 11 to remain afloat through variations in water level. In the preferred embodiment hose 13 is a conventional high pressure hydraulic hose with couplings at the ends. An antenna 14 is mounted atop buoy 11 with shaft 15 in buoy 11 providing a passageway between the antenna base and hose 13 so that transmission lines 17 can be connected between antenna 14 and sample unit 12. As shown in FIG. 2, sample unit 12 houses the mechanisms forming the majority of the present invention. Sample unit 12 is composed of three sections: base 18, midsection 19 and top 20. The base 18 contains batteries 21 which power the control module 22 occupying the center and bottom of cylindrical midsection 19. In the preferred embodiment, the batteries 21 are standard twelve volt automotive batteries of the conventional sealed, no maintenance design. Together, batteries 21 have an output of 96 volts. Control module 22 is an integrated unit containing a conventional data processor, transmitter, receiver and activation system well-known in the art. The functions of the control module are described hereinafter under the operation of the present invention.

Figure 4:
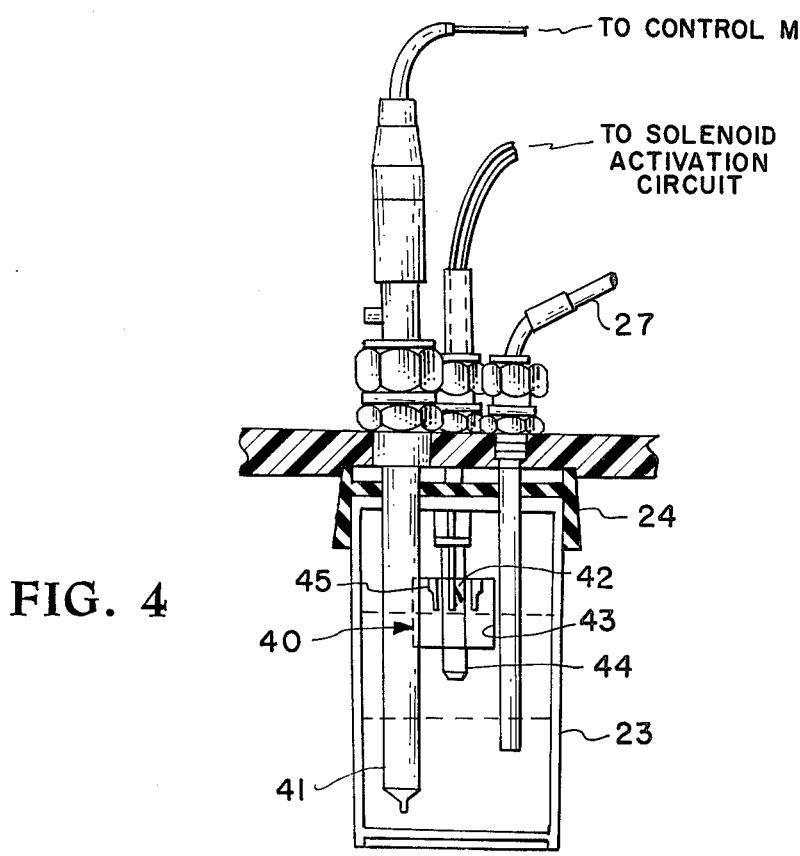
FIG. 4 is an enlarged section of a single sample chamber.

Positioned radially about the hollow center 65 of midsection 19 and seated in cavities within the foam insulation are a plurality of removable sample chambers 23 which number ten in the preferred embodiment the tops of which terminate at the intersection of sample unit midsection 19 and top 20. As shown more clearly in FIG. 4, each sample chamber 23 has a top seal 24 sealing its volume until sample unit 12 is disassembled. In the preferred embodiment, each sample chamber 23 is a polymethylpentene straight side wide mouth jar while each top seal 24 is a polypropylene screw closure, both the jars and the closures being noncontaminating and autoclavable for sterilization.

As shown in FIG. 2, apparatus which performs the sampling function of the present invention occupies top section 20 of sample unit 12. Located radially about top 20 are a plurality of spool valves 25 which pierce and attach to the outer surface of top 20 and extend inwardly toward a cylindrical inner wall 26. The spool valves are equal in number to the sample chambers, each being matched with one of the other, and connected thereto by a supply tube 27. The spool valves are further matched in number by solenoids 28 attached to the inner surface 29 of inner wall 26, the plunger 30 of each extending therethrough to operatively connect with its matching spool valve 25.

Figure 3:
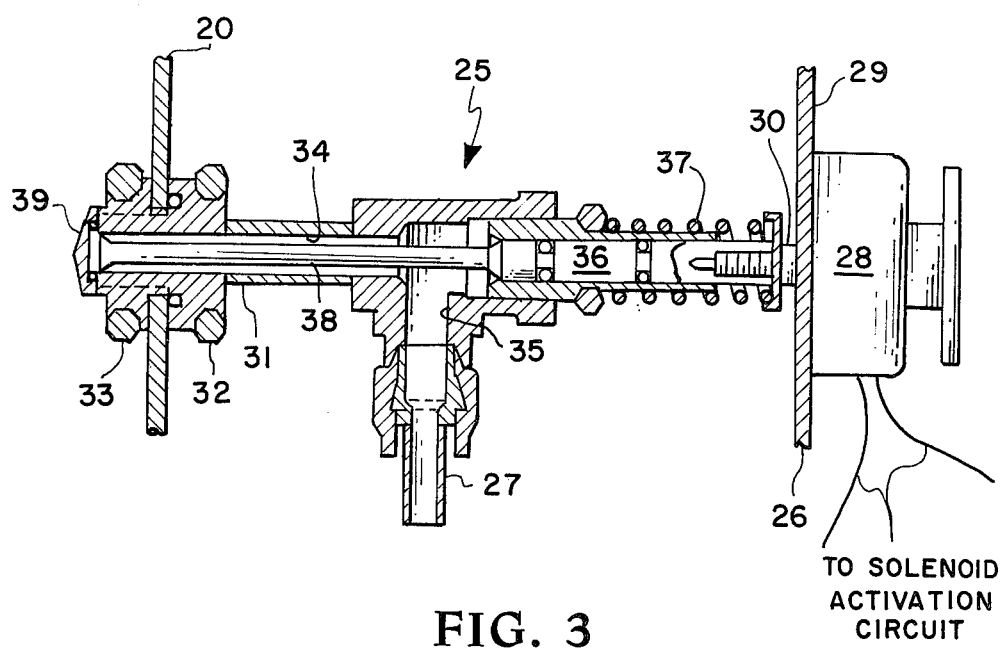
FIG. 3 is an enlarged section of a single valve assembly.

Each spool valve 25 is constructed as shown in FIG. 3. Valve barrel 31 extends through the outer wall of top 20 and attaches thereto by an inner and outer nut 32 and 33, respectively. Valve barrel 31 defines a cylindrical feeder passageway 34 extending throughout its length intersected by a supply orifice 35 extending to supply tube 27 connected to a sample chamber 23 as shown in FIG. 2. A piston 36 occupies a portion of the feeder passageway 34 behind supply orifice 35 and is held in the normal position by a spring 37. Plunger 30 of solenoid 28 is threadedly connected to piston 36 and upon activatin of solenoid 28 forces piston 36 to travel toward the outer wall of top 20. The translation of piston 36 from the normal to the activated position is confined to the length of feeder passageway 34 extending behind orifice 35, thereby assuring that feeder passageway 34 is always in communication with supply tube 27. Spool shaft 38, having a cylindrical configuration of a diameter less than passageway 34, occupies the remaining length of passageway 34. Spool shaft 38 is operatively connected to piston 36 at one end and is flared with a cap 39 at the other end in such a manner that when piston 36 is in the normal position, the flared end fills and seals passageway 34 while cap 39 seats against and covers the outer extremity of barrel 31. Thus, in the normal position spool shaft 38 closes valve 25 and eliminates any end cavity about barrel 31.

When piston 36 translates to the activated position through the impetus of plunger 30, spool shaft 38 and end cap 39 are forced outward into the water body surrounding sample unit 12, thereby opening passageway 34 for the ingress of a water sample.

While spool valve 25, as described, operates much as any other valve, its design has several unique attributes which lends it to sampling applications. Since valve barrel 31 extends into the surrounding water while spool shaft 38 and cap 39 fit flush against the end of barrel 34, no cavity is present which would allow the accumulation of a stagnant water volume about valve 25. Thus, the present invention assures that the water sample taken is representative of the water body at the time when taken. Furthermore, should sample unit 12 remain submerged for an extended period, conducive to the growth of marine organisms on its surface, the outward motion of cap 39 removes any such accumulation from the valve end, again assuring the representativeness of the water sample.

As previously mentioned, a water sample taken through spool valve 25 is communicated to its related sample chamber 23. In order for sample analysis to be possible, apparatus for water specimen ingress, volume control and property analysis must be available within the sample chamber. In the preferred embodiment shown in FIG. 4, this apparatus includes supply tube 27, level switch 40 and sensor 41. A water sample entering chamber 23 through supply tube 27 causes ball 43 of level switch 40 to rise along rod 44 so that upon reaching a predetermined level, permanent magnets 45 residing in ball 43 trip a conventional reed-type switch 42 in rod 44 causing power to the solenoid 28 to be cut resulting in the closing of spool valve 25. In the preferred embodiment, level switch 40 is a Gems LS-42295 single station level switch LS-3 series from Delavel Turbine, Inc., Gems Sensors Division, Farmington, Conn. 06032.

As previously mentioned, control module 22, an integrated unit of conventional design, controls all sampling unit functions and provides a communications link with the on-shore sending and receiving station 46.

Figure 5:
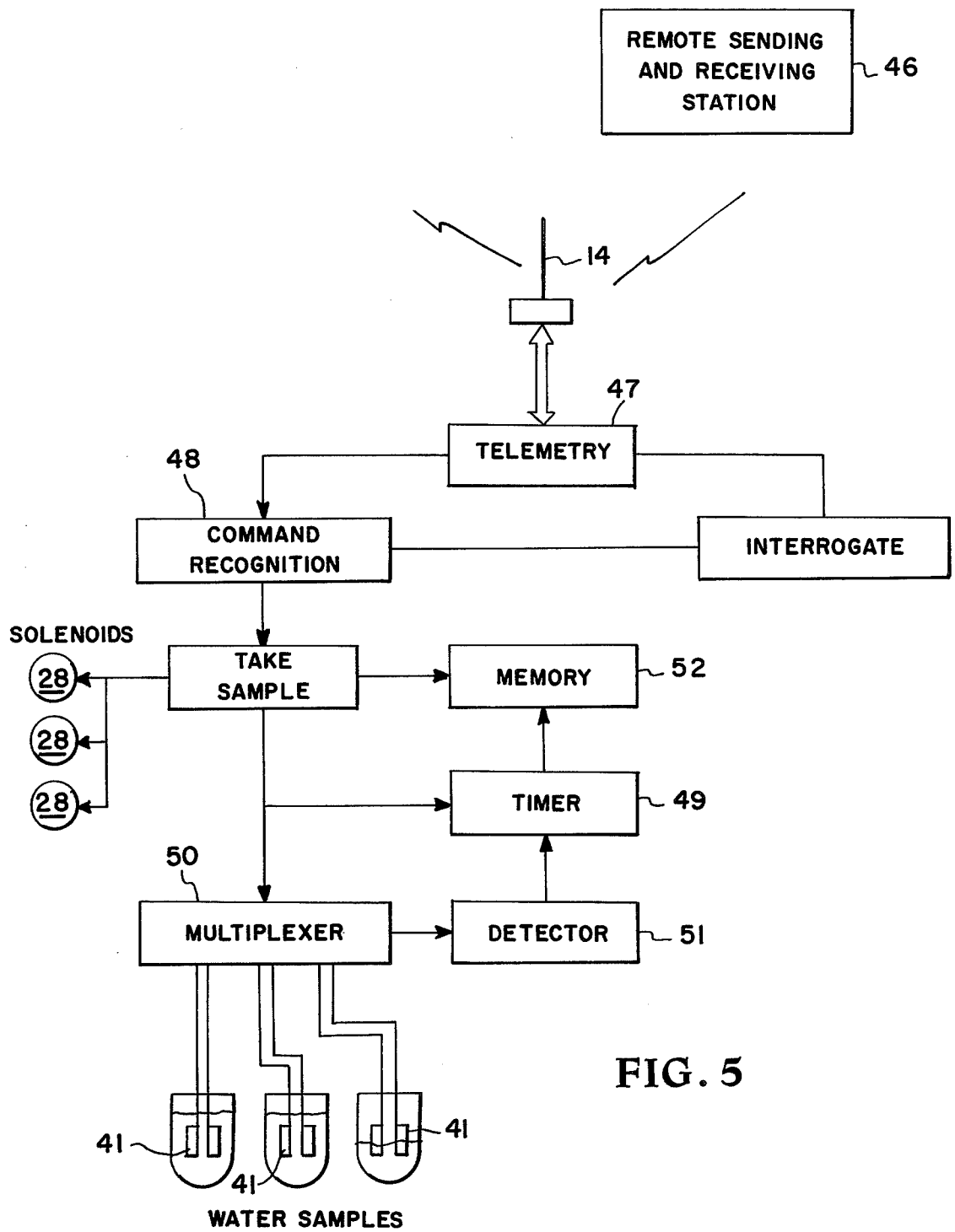
FIG. 5 is a block diagram of the sampling unit control module.

A block diagram of control module 22 is presented in FIG. 5. The telemetry unit 47, a conventional VHF transceiver, receives signals broadcast by sending and receiving station 46 through antenna 14 and transmission lines 17, which are transferred to command recognition unit 48. Command recognition unit 48 differentiates between two major signal types: a "take sample" signal and an "interrogate" signal. Each "take sample" signal causes control module 22 to activate one solenoid 28, then index to the next solenoid 28 which will be activated upon receipt of the next "take sample" signal. This solenoid activation continues until all solenoids 28 have been activated. The receipt of each "take sample" signal by command recognition unit 48 also causes it to start timer unit 49 for that particular sample.

Sensors 41 provide a voltage reading for each sample to a multiplexer 50 which in turn passes its readout to a detector 51. The detector 51 monitors the sample readout and, in the preferred embodiment, causes timer 49 to run backwards for each particular sample that has experienced a voltage change of 30 millivolts until a voltage change of 90 millivolts is realized at which time detector 51 causes timer 49 to stop for that sample. The timer 49 continuously updates memory unit 52 with the time for each sample and, once stopped for a particular sample, also registers a "completed" code in memory unit 52 for that sample.

Upon receipt of an "interrogate" signal by telemetry unit 47, it causes the time data and "completed" codes for each sample stored in memory unit 52 to be transferred to telemetry unit 47 where it is broadcast to remote sending and receiving station 46.

In the preferred embodiment, the materials used to fabricate the portions of the actual sampling apparatus that come in contact with the samples taken were chosen based upon their ability to be sterilized to prevent sample contamination. Thus, valves 25 and sampling unit top 20 may be aluminum, stainless steel, or the like, tubing is laboratory grade polypropylene, level switch 40 is polysulfone and sample chambers 23 are polymethylpentene, all of which are autoclavable. The remainder of sampling unit 12 is constructed of aluminum or stainless steel and, when fully assembled, the sampling unit weighs approximately 800 pounds.

OPERATION

Once a water body of interest is identified and its depth determined, a remote water monitoring system is deployed having a connecting tube 13 of the proper length. The control module 22 is set to first activate the solenoid 28 associated with a desired sample chamber 23 in response to a telemetry command from on-shore sending and receiving station 46; then index to the next solenoid in a clockwise direction. The transmission link is through conventional VHF transceivers, one being integrated into telemetry unit 47 of control module 22, using tone modulation commands received by antenna 14 and transferred to control module 22 by transmission lines 17.

Control module 22 is pre-set so that the first solenoid 28 to be activated is known and subsequent solenoid activation is in a specified sequence. Hence, each water sample can be identified when sample unit 12 is retrieved.

A "take sample" command causes control module 22 to activate the first solenoid 28 causing its plunger 30 to extend outwardly toward the outer wall of top 20. The plunger 30 forces piston 36 to move from the normal to the activated position causing spool shaft 28 to extend into the surrounding water body thus unseating cap 39 and the flared end of the spool shaft from the end of the valve barrel 31. The difference in diameters of spool shaft 38 and feeder passageway 34 allows water to communicate through passageway 34, into supply orifice 35 to pass into sample chamber 23 from supply tube 27.

As water volume within sample chamber 23 increases, ball 43 of level switch 40 rises along rod 44 to a predetermined level whereupon switch 42 is tripped by permanent magnets 45 cutting power to solenoid 28. Upon deactivation of solenoid 28, piston spring 37 forces piston 36 to return to its normal position, bringing with it spool stem 38. The inward motion of spool stem 38 causes its flared end to fill the end of feeder barrel 34 and causes cap 39 to seat against the end of valve barrel 31 thus closing spool valve 25. The control module 22 then indexes so that it will activate the next solenoid upon a "take sample" command.

In the preferred embodiment, the presence and quantity of coliform bacteria in each sample is detected by sensor 41. Where this analysis is desired, each sample chamber 23 is innoculated with a known quantity of lauryl tryptose nutrient broth before sample unit 12 is sealed and deployed. Following the method discussed in U.S. Pat. No. 4,009,078, sensor 41 is comprised of a standard calomel electrode (SCR-Beckman Instrument, Inc., Fullerton, Calif.) as a reference electrode and a platinum electrode as the measuring electrode. A suitable electrically actuated circumferentially disposed strap type heater 55 is provided within midsection 19 so as to be in contact with each sample chamber 23 and serves to maintain thermal control of the nutrient broth therein. The lead wires for heater 55 and the other electrical leads needed extend from control module 22 through the hollow center 15. The sensor 41 identifies the production of hydrogen, a characteristic by-product created by consumption of the nutrient broth, by coliform bacteria, as a potential change in the sample chamber. The number of organisms originally present in the sample is directly proportional to the time required for the electrochemical process to produce a known voltage level. The time interval between the time a sample is taken and the voltage level reached (lag time) is determined by control module 22 and stored for later transmission.

The control module will continue to index from solenoid to solenoid in a clockwise fashion as each "take sample" command is received until all sample chambers are filled. To reduce the power drain on the batteries 21 the control module 22 in the preferred embodiment transmits data only upon the commmand "interrogate", giving the current status of the contents of each sample chamber.

Although the invention has been described relative to a specific embodiment thereof, it is not so limited and many modifications and variations thereof will be readily apparent to those skilled in the art in the light of the above teachings. For example, although the sensor 41 of the preferred embodiment indicates only the quantity of coliform bacteria in each water sample, clearly other sensors can be utilized to determine other pertinent properties. Also it is possible to both set the level switches 40 to alter the quantity of the samples to be taken and to program the control module to take two or more samples simultaneously. These and other variations in the present invention will be readily apparent to those skilled in the art without departing from the spirit and scope of the present invention. It is therefore to be understood that within the scope of the appended claims the invention may be practiced otherwise than as specifically described.

What is claimed as new and desired to be secured by Letters Patent of the United States is:

1. A remotely operated water monitoring system for obtaining a series of representative water samples taken at desired time intervals in a body of water comprising, in combination:
  a remote sending and receiving station for sending and receiving signals above the surface of the water body;
  means for transmitting signals from said station into the water body;
  a sterile watertight sample unit adaptable for lowering into the water body;
  a plurality of chambers within said sample unit for the receipt and storage of water samples in a controlled environment;
  delivery means for admitting representative water samples to each said chamber;
  means for activating said delivery means;
  means for controlling the volume of each sample taken;
  means for analyzing each sample taken for a specific property and producing data thereon; and
  control means for receiving and transmitting signals and differentiating between at least two types of signals so received, receipt of the first type of said signals each time triggering said means for activating said delivery means for only one said sample chamber, the triggering being in a sequential pattern until each of said plurality of receptacles contains a water sample; while the receipt of the second type of said signals each time causes said control means to receive said data from said analysis means and transmit information thereon to said remote sending and receiving station.

2. The water monitoring system of claim 1 wherein said remote sending and receiving station comprises a VHF transceiver using tone modulation to differentiate generated signals.

3. The water monitoring system of claim 1 wherein said means for transmitting said signals into the water body is comprised of a floating buoy having an antenna attached to the top thereof with transmission lines running to said sample unit and connected with said control means therein.

4. The water monitoring system of claim 1 wherein the means for delivery of a representative water sample to each said receptacle includes:
  a plurality of valve assemblies positioned about the periphery of said sampling unit extending therethrough and terminating beyond the surface of said sampling unit thereby eliminating any cavity thereabout, said valve assemblies being equal in number to said sample chambers and including:
    a. a barrel defining a cylindrical passageway open at the external end of said valve assembly;
    b. a piston within said passageway and being reciprocal between a normal and an activated position;
    c. means to return and hold said piston in said normal position;
    d. a spool shaft within said cylindrical passageway of a diameter less than said passageway operatively connected to said piston and having both a flared end and a cap which, when said piston is in said normal position, respectively seal said passageway to prevent water ingress and cover said valve barrel to prevent marine organisms from growing thereon and which, when said piston is in said activated position, extend into the water body to respectively allow water to enter said passageway and remove any marine growth from about said valve barrel whereby a representative water sample is obtained; and
    e. a tube piercing said valve barrel and opening as an orifice in the portion of said passageway occupied by said spool shaft when said piston is in said activated position, extending therefrom to one said receptacle whereby water entering said passageway is communicated to said receptacle.

5. The remotely operated water monitoring system of claim 1 wherein the means for activating said delivery means includes a plurality of solenoids each having a plunger operatively connected to one of said pistons within said valve barrels such that upon activation of said solenoid by said control means said piston moves from said normal to said activated position.

6. The remotely operated water monitoring system of claim 1 wherein the means for controlling the volume of each sample includes for each said sample chamber:
a hollow rod extending into said chamber and containing a switch the position of which is variable to coincide with the level of the volume of water desired to enter said receptacle;
a ball float containing permanent magnets encircling said shaft and able to translate therealong to correspond with the level of water entering said chamber, said magnets activating said switch when said water reaches the desired level;
communication means between said reed switch and said control means such that the activation of said reed switch causes said control means to deactivate said solenoid and allowing said return means to move said piston to the normal position whereby said valve assembly is closed.

7. The remotely operated water monitoring device of claim 1 wherein the means for analyzing each said sample for a specific property detects the presence and quantity of coliform bacteria.

* * * * *